United States Patent
Lewis (10) Patent No.: US 9,504,601 B1
(45) Date of Patent: Nov. 29, 2016

(54) CLOSED CIRCUIT FORCED HOT AIR INTRAOPERATIVE PATIENT WARMER WITH IMPROVED STERILITY

(71) Applicant: Randall J. Lewis, Bethesda, MD (US)

(72) Inventor: Randall J. Lewis, Bethesda, MD (US)

( * ) Notice: Subject to any disclaimer, the term of this patent is extended or adjusted under 35 U.S.C. 154(b) by 0 days.

(21) Appl. No.: 15/056,120

(22) Filed: Feb. 29, 2016

(51) Int. Cl.
*A47C 21/00* (2006.01)
*A61F 7/00* (2006.01)

(52) U.S. Cl.
CPC ...... *A61F 7/0097* (2013.01); *A61F 2007/0055* (2013.01)

(58) Field of Classification Search
CPC .. A61F 2007/006; A61F 7/0097; A61F 7/00; A61F 2007/0055; A61F 2007/0069; A61M 37/00; A61N 5/06; A61G 2210/90; A61L 9/00; A61L 9/14
See application file for complete search history.

(56) References Cited

U.S. PATENT DOCUMENTS

| | | | | |
|---|---|---|---|---|
| 1,121,227 A | 12/1914 | Mitchell | ........ | 156/533 |
| 2,259,712 A | 10/1941 | Sweetland | ........ | 5/421 |
| 2,504,308 A | 4/1950 | Donkle | ........ | 62/261 |
| 2,753,435 A | 7/1956 | Jepson | ........ | 126/204 |
| 2,978,225 A | 4/1961 | Dallas | ........ | 165/46 |
| 4,094,357 A | 6/1978 | Sgroi | ........ | 165/104.26 |
| 4,132,262 A | 1/1979 | Wibell | ........ | 165/206 |
| 4,777,802 A | 10/1988 | Feher | ........ | 62/3.3 |
| 4,884,304 A | 12/1989 | Elkins | ........ | 5/421 |
| 5,318,568 A * | 6/1994 | Kaufmann | ........ | A61F 7/00 285/320 |
| 5,968,084 A | 10/1999 | Augustine et al. | ........ | 607/107 |
| 7,114,204 B2 | 10/2006 | Patrick | ........ | 5/81.1 R |
| 7,837,721 B2 | 11/2010 | Augustine et al. | ........ | 607/96 |
| 8,414,671 B2 | 4/2013 | Augustine et al. | ........ | 55/358.2 |
| 2003/0208251 A1* | 11/2003 | Papay | ........ | A61F 7/00 607/107 |
| 2010/0234794 A1* | 9/2010 | Weadock | ........ | A61G 13/108 604/20 |

* cited by examiner

*Primary Examiner* — Kaitlyn Smith
*Assistant Examiner* — Yasamin Ekrami
(74) *Attorney, Agent, or Firm* — Ernest D. Buff & Associates, LLC; Ernest D. Buff, Esq.; Margaret A. LaCroix, Esq.

(57) ABSTRACT

A system for a closed circuit forced hot air warmer of patient beds and blankets with improved sterility has a patient mattress or blanket microprocessor controlled warmer that circulates heated air in a closed system without releasing warmed air into the area surrounding the patient or into the operating room. The system helps to avoid the exposure of patients and hospital workers in the operating room to possible infecting microbes carried in unsterile turbulent air currents related to the release of air from non-closed systems. The machinery and flexible hoses of the system are initially sterilized by a microprocessor controlled antimicrobial mist generator. The system does not discharge jets of warmed air due to the closed circuit arrangement. Turbulent air flow previously produced in the vicinity of the patient by high velocity air jets is eliminated. An ambient, quiescent condition accorded by closed circuit heating prevents infection of patients and operating room personnel by microbe migration.

9 Claims, 6 Drawing Sheets

CLOSED CIRCUIT FORCED HOT AIR INTRAOPERATIVE PATIENT WARMER WITH IMPROVED STERILITY

FIELD OF THE INVENTION

The present invention relates to thermal blankets; and, more particularly, to a system employing forced heated air in a closed circuit within a thermal blanket or mattress, warming the patient and preventing hypothermia, while maintaining the sterility of the operative area on the patient.

DESCRIPTION OF THE PRIOR ART

Numerous prior art patents and disclosures relate to warming of a patient mattress or blanket by the passage of warmed fluids. Warmed fluids may be heated water or heated air. If the fluid-tilled device leaks or ruptures, the heated water disadvantageously creates puddles of leaked water around the patient and on the operating room floor. Water filled blankets are heavy and the patient may find these blankets highly uncomfortable. Mattresses and blankets that circulate warm air discharge the air through a plurality of exit passages in the form of high velocity jets. The discharge creates turbulent circulation currents in the room air that can pick up microbes in floor dust and deliver them to the patient's operative area, as well as hospital room workers, U.S. Pat. No. 1,121,277 to Mitchell discloses a warming appliance for beds. This warming apparatus circulates warm water. The disclosure of this patent shows the bed having a plurality of pipes through which heated water is circulated. A hot water heater or boiler is connected to a pipe that feeds the bed heating pipes. Warm air is not circulated through the bed.

U.S. Pat. No. 2,259,712 to Sweetland discloses a bed warmer apparatus. A fan blows air through an electric heater and the warmed air is passed through a pipe in the bed. The bed warmer requires power to drive the blower motor. A flexible hose conveys warm air to the cushion, which serves the double purpose of supporting the bed cover and providing warmth in the bed. A conventional type of bed cover is used. The blower passes air over electrical heaters to warm the air, which is passed through pipes in the bed. The warm air is not returned to the blower since this is not a closed system. Release of the warm air can cause currents of unsterile air, containing bacteria, to surround the patient or the operative site, increasing prospects for infections.

U.S. Pat. No. 2,504,308 to Donkle discloses a heating and cooling cover. The bed has a heating or cooling cover supplied with a working fluid from a refrigerator or a heat pump. The cover does not have warm air circulating in a closed system. A working fluid is returned to the refrigeration or heat pump system through a heat exchanger, which heats or cools the area adjacent to the refrigeration or heat pump unit. The process creates turbulent air currents that can pick up floor dust and microbes and deliver them the patient and the operating room workers.

U.S. Pat. No. 2,753,435 to Jepson discloses a thermal blanket. The thermal blanket is on a bed and is provided with a fluid circulating unit. The fluid circulating unit provided with a knob to adjust the temperature of the thermal blanket. The fluid is indicated to be distilled water. The device disclosed by the Jepson patent does not circulate warm air within the blanket.

U.S. Pat. No. 2,978,225 to Dallas discloses a thermal blanket. The thermal blanket is provided with tubes through which liquid is circulated. The thermal blanket has a plurality of fluid passage ways disposed in a parallel relationship. The edge includes a liquid distribution manifold unit. The thermal blanket does not circulate warm air in a closed circuit to provide warmth to the patient.

U.S. Pat. No. 4,094,357 to Sgroi discloses a heat transfer blanket. The heat transfer blanket has a plurality of flexible sheath heat pipes that provide a uniform heating or cooling pattern therein. The ends of the flexible heat pipes that are free from the blanket are thermally coupled to a combination heating and cooling system. When utilizing the heating system, the flexible heat pipes provide elevated temperatures at the blanket surfaces. When utilizing the cooling system, the flexible heat pipes provide lower than ambient temperatures at the blanket surfaces. A solid metallic rod is affixed to one end of the pipe. A wick extends the entire length of the interior of the pipe, which is partially filled with a liquid that becomes a vapor upon sufficient heating. The end of the pipe in which liquid is situated accepts heat from the surrounding area, causing the liquid to vaporize. The vapor ultimately communicates with the other end of the pipe. At this end, cooling effects are introduced and the vapor condenses back to a liquid state. Liquid then travels along the wick to the end of a tube containing the liquid. The efficiency of thermal coupling between opposite ends of the heat pipe is substantially higher than the coupling efficiency of an equivalent diameter and length of a solid copper rod. The heat transfer means for warming or cooling the blanket is by evaporation heating or cooling of liquid contained in the wick. Warm air is not passed within pipes in the heat transfer blanket in a closed circuit.

U.S. Pat. No. 4,132,262 to Wibell discloses a heating and cooling blanket. This cooling and heating blanket has a blanket enclosure with heating means including a plurality of flexible elements positioned within the enclosure for being electrically energized to supply heat to the enclosure so that the enclosure may be retained above room temperature. A cooling means includes a plurality of flexible fluid carrying conduits positioned within the enclosure through which a heat transfer fluid can flow, such that the enclosure may be retained below room temperature. Control means including an electric motor and a pump driven thereby are located remotely relative to the enclosure. A flexible conduit means connects the enclosure and the cooling means. A regulating means is operatively associated with the heating means and the cooling means. The regulating means is adapted to energize the control means or the heating means in response to increases and decreases of the temperature associated with the enclosure. With this arrangement, the temperature of the blanket may be retained above or below the room temperature in which the blanket is located. The heating and cooling means are separate from each other. The heating means comprises electrical heating wires, which are heated by the passage of an electrical current. Heating of the blanket is not achieved by the passage of warm air in a closed circuit.

U.S. Pat. No. 4,777,802 to Feher discloses a blanket assembly and selectively adjustable apparatus for providing heated or cooled air thereto. This blanket assembly has an outer layer constructed of a relatively close weave fabric preventing air flow there through. Underneath the top layer is a second layer of material edge connected to the top layer and which is constructed of a material permeable to air, such as relatively thin taffeta, for example. A cavity between the two layers receives pressurized cooled or heated air that passes through the air permeable layer to cool or heat the individual using the blanket assembly. A modified blanket assembly construction includes rigid edge wall members holding the outer and inner layers separated at a predetermined spacing. This reduces "pinch-off" between the layers that would restrict airflow within parts of the cavity or chamber. Peltier effect elements are selectively energizable to heat or cool air provided to the blanket assembly cavity. The heating/cooling of the patient bed is effected by a closed circuit with a solid state PN junction to create the heating/cooling based on the Peltier effect. Passage of direct current in one direction causes one PN junction to heat while the other junction cools. The heated PN junction supplies heat to warm the patient bed while the coolness of the other junction is discharged in air surrounding the patient as well as the operating room. This discharge of cooled/warmed air stirs microbes and floor dust in the room, creating the possibility of infecting the patient and workers in the operating room. The device disclosed by the Feher patent does not use circulation of warm air in a closed system to warm the bed of a patient.

U.S. Pat. No. 4,884,304 to Elkins discloses a bedding system with selective heating and cooling. This bedding system has provision for heating or cooling a person and for applying the heating or cooling only in areas of the bed where the person is located. A sealed three-ply heat transfer and insulating device covers the mattress, below the contour sheet or other covering which comes in contact with the person's body. A wicking contour sheet or other cover capable of absorbing any condensation on the surface of the three-ply device may optionally be used. Between the lower two plies of the three-ply material is channeled a flow of coolant liquid at a regulated temperature that are close to human skin temperature. Above these two plies, i.e. between the middle ply and the upper ply, is a seated envelope containing slightly pressurized air. A tight weight, well-insulated comforter is also recommended to isolate the sleeper from the thermal ambient environment. The bedding system includes a temperature control unit and a mattress cover device, which is positioned over a mattress. The mattress cover device includes liquid flow channels and preferably a gas envelope or plenum space located above the liquid flow channels. The multiplicity of liquid flow channels is interconnected to form one or more circulation paths. The mattress is heated by liquid flow channels. It is not heated by the passage of warm air flowing in a closed circuit.

U.S. Pat. No. 5,968,084 to Augustine et al. discloses a thermal blanket. This thermal blanket includes an inflatable covering with a head end, a foot end, two edges and an undersurface. The covering is inflated through an inlet the foot end by a thermally-controlled inflating medium. An aperture array on the undersurface of the covering exhausts the thermally controlled inflating medium from the covering. Exhaust port openings are provided at the edges of the covering to vent the inflating medium, which enhances circulation of the thermally-controlled medium through the cover. An uninflatable section is provided at the head end, together with an absorbent bib attached to the covering, adjacent the uninflatable section. An uninflatable section may also be provided at the foot end having a pair of seams to form an erectable drape section. When inflated, the thermal blanket self-erects and provides a bath of thermally-controlled inflating medium to the interior of the erected structure. The enhanced circulation of the medium through the covers maintains a relatively high average temperature under the blanket and a relatively uniform distribution of temperature in the inflating medium which is exhausted through the apertures into the structure's interior. When the structure covers a patient, the uninflatable section at the head end provides a relatively unobstructed view of the patient's face, while the absorbent bib maintains a relatively sanitary environment in the area beneath the patient's head. The uninflatable section at the foot end retains heat from the inflating medium to warm the patient's feet and insulate the bare skin of the feet from excessive conductive heat from the hose connected to the inflation inlet. The thermal blanket may be sized to cover selected areas of a patient such as the upper body, including the chest, arms, or shoulders, or the lower body, including the pelvic and groin area and the legs. The warmed air is exhausted underside of the thermal blanket through the apertures provided. The flow of warn air through the apertures occurs at high velocity, thus bringing microbes and dust to the patient by turbulent movement of ambient air flow.

U.S. Pat. No. 7,114,204 to Patrick discloses a method and apparatus for transferring patients. This patient transfer apparatus includes an inflatable mattress, alternatively with a rigid top board with a patient restraint system which a patient can be placed, when patient immobilization is required. A portable cart is included with a chamber for storage of a plurality of mattresses. The cart also has a gas/air blower and power supply system for empowering the blower. The power system includes provision for drawing power from line AC/DC, and has a rechargeable battery and charger for maintaining the battery by connecting the supply to the line AC/DC. The mattress has a perforated bottom surface for exit of air to provide an air cushion, and is constructed with a white top surface and a dark bottom surface for optimum recognition of contamination, and identification of the bottom, which must be placed downward. The cart is coated with an antimicrobial substance to minimize the risk of contaminants. As shown in the first figure, the patient 90 has been placed on an inflatable mattress 22 for providing an air cushion 96, and the supply system 18 has the hose 26 connected to the air mattress 22 and is supplying a gas, a portion of which is forced out exit holes 82, causing the air mattress 22 to float on a cushion of air/gas 96. An attendant can at this stage, move the air mattress 22 with patient over onto the bed 94. The air mattress disclosed by the Patrick patent s supplied with pressurized air or gas to support the patient lying on the bed. A plurality of holes in the mattress provides on the opposite surface to the one over which the patient is lying, an egress for high velocity air/gas jets which, in turn, provide an air cushion, enabling the bed with the patient to be slid from one location to the other. The air of gas jets provides very strong turbulent air currents stirring up dust and microbes that can infect the patient as well as hospital workers in the operating room. This apparatus is not heated by warm air with a closed air circulation system.

U.S. Pat. No. 7,837,721 to Augustine, et al. discloses a patient comfort apparatus and system. This apparatus and system thermally comforts a patient; and includes a clinical garment such as a hospital gown, robe, bib, and other equivalents provided with pneumatic, convective thermal treatment for persons or animals. The pneumatic convective device provides convective warming focused or directed primarily on the thorax or body core. The pneumatic convective device includes at least one inlet accessed through a clinical garment, a region in distribution with the inlet for distributing a stream of pressurized, thermally treated air, and a permeable member for emitting pressurized, thermally treated air from the distribution region. As shown in FIG. 1A, the sheets 114 and 116 form between themselves a pneumatic structure to receive and distribute pressurized air within itself. At least one permeable member of the device (the sheet 114, for example) cooperates with the pneumatic structure to emit pressurized air from the device. In this regard, one end of an air hose may be received through an inlet port 127. A stream of pressurized, thermally conditioned air introduced through the air hose fills the space between the sheets 114 and 116 and is distributed throughout the space. The pressurized air is emitted from the pneumatic structure through the air permeable sheet 114. Motion of the emitted air supports heat transfer with a body adjacent, next to or near the pneumatic structure facing the permeable sheet 114. The permeable sheet has holes that deliver the pressurized warm air at high velocity, producing turbulent airflow adjacent to the patient, bringing dust and microbes to the patient U.S. Pat. No. 8,414,671 to Augustine, et al discloses personal air filtration devices for use with bedding structures. These devices, methods and systems create a zone of filtered air proximate a patient's head, They include an air filtration device having a blower configured to be disposed within, below, or affixed to a bedding structure; an air plenum in flow communication with the blower and in support of the head of the user and having an air delivery surface configured to distribute the air flow to the zone of filtered air; and a filter disposed within the device for filtering the air flow before it is distributed to the zone of filtered air. Filtered air is exhausted, surrounding the patient and producing airflow that is turbulent and can deliver microbes and dust to the patient.

Based on the foregoing, there exists a need in the art for an inexpensive single use system for a closed circuit forced hot air warmer for patient beds and blankets that provides improved sterility, thereby preventing infection of the patient as well as operating room hospital workers.

SUMMARY OF THE INVENTION

The present invention provides a system for a closed circuit forced hot air warmer of patient beds and blankets with improved sterility. A warmer circulates heated air within a patient mattress or blanket in a closed system, without releasing warmed air into the area surrounding the patient or into the operating room, thereby preventing the possibility of patients suffering infections from being exposed to unsterile air currents containing microbes Briefly stated, the closed circuit forced hot air warmer provides hot air for warming a patient bed or blanket, preventing hypothermia of the patient that may significantly increase healing time periods. Warm air is supplied from a blower, the inlet and outlet ports of which are guarded with a HEPA filter having a pore dimension less than 0.22 microns to prevent the entry of microorganisms or dust particles. The temperature of warm air, its pressure and flow rate are controlled by a control panel set by the operator of the device. When used to warm the bed of the patient, the air pressure within the mattress helps to support the patient's body weight. Being a closed system, the pressure can be readily increased according to the weight and size of the patient. The flow rate determines how quickly the warmed air is delivered to the patient, and is related to the rotational rate of a blower motor.

In its preferred embodiment, the system for closed circuit forced hot air warming of patient beds and blankets with improved sterility comprises:

a blower with controlled air heating capability having an input and an output opening, each opening being provided with a HEPA filter;

b) said HEPA filters having pore openings less than 0.22 microns capable of filtering microbes and dust particles;

c) said output opening being connected to an input connection of a bed or blanket using a flexible hose with quick release connector;

d) said patient bed or blanket having an output that connects the exiting warm air to the input of said blower, said connection being made with a flexible hose and quick release connector;

e) the entire flow path of warmed air being a closed circuit with no discharge of warmed air surrounding the patient within the operating room;

f) a flexible hose able to connect to an antimicrobial mist generator with a quick release connector;

g) said antimicrobial mist generator being connectable to the return blower with a quick release connector;

h) said antimicrobial mist a being detached during warming of the patient bed or blanket by passage of warm air from said blower; and i) said antimicrobial mist generator, connected to the blower by the output and return hose, can be tuned on after a safe disposal step for said patient bed or blanket;

whereby said system for said closed circuit forced hot air warmer of patient beds and blankets with improved sterility is cleaned internally by a vaporized disinfectant, preventing the microbial contamination of the apparatus, as recommended by the FDA, and thereby discouraging operative patient infections when the heater is employed during surgery.

BRIEF DESCRIPTION OF THE DRAWING

The invention will be more fully understood and further advantages will become apparent when reference is had to the following detailed description of the preferred embodiments of the invention and the accompanying drawing, in which.

DETAILED DESCRIPTION OF THE INVENTION

The objective of the invention is to provide warmth to a patient by a warmer that circulates heated air within a patient bed or blanket in a closed system without releasing warmed air into the area surrounding the patient or in the operating room, thereby preventing the possibility of patients suffering infections and hospital workers in the operating room being exposed to infecting microbes.

Measurements have shown that a patient on a hospital bed loses about 1.6 degrees C. body temperature during the first hour. Such body temperature loss can lead to hypothermia, shivering and may compromise the patient's healing ability, [See http://solutions.3m.com/wps/portal/3M/en_EU/Healthcare-Europe/EU -Home/Products/InfectionPrevention/Patient_Warming/.] Patient warming beds and warming blankets are essential to prevent this onset of patient hypothermia.

For the past two decades, maintenance of patient body temperature during surgery has largely been achieved with forced hot air warming; this process replaced circulating hot water blankets, which were cumbersome and often ruptured, covering the floor with water. Tent, blanket and mattress designs have also been used. Virtually all of these have been inexpensive and disposable, and have attempted to avoid the problem of difficult and often incomplete cleaning between uses. All of the currently used forced hot air devices have a blanket or pad with multiple holes that emit the warmed air around the patient or an open tent over the patient into which the warm air is blown. Some recent studies have documented that the release or leakage of the forced air causes unwanted air currents that bring up potentially unclean air from near the floor or cause increased numbers of particles and bacteria to circulate over the prepped area of the surgical incision, increasing the risk of operative infection. Examination has also revealed bacteria collecting within the blowers. Another study demonstrated that the air currents interfere with the laminar airflow sometimes used in the operating room to discourage bacterial contamination. The FDA has also recently released an alert, describing their concerns and the need for a regular program of cleaning and maintenance of heater/cooler devices. While the contention that these devices are related to an increase in operative infections has been questioned, it seems reasonable to attempt to avoid air leakage and any possibly undesirable air currents that might increase infection risk. Avoiding the buildup of bacteria within the blower is obviously a reasonable goal. Bacterial contamination related to increased infection has recently been reported in the liquid of water blankets. Staying with a forced hot air system that employs inexpensive, disposable mattresses and blankets that do not need to be cleaned is clearly desirable.

Recently FDC has issued the following warning located at http://www.medscape.com/viewarticle/852750 which is reproduced below:

FDA Warns Infections a Risk With Heater-Cooler Devices

Megan Brooks

Disclosures | Oct. 15, 2015

The use of heater-cooler devices has been associated with nontuberculous mycobacterium (NTM) infections, primarily in patients undergoing cardiothoracic surgeries, the US Food and Drug Administration (FDA) warned today.

Heater-cooler devices are used during medical and surgical procedures to warm or cool a patient, as appropriate. The devices include water tanks that provide temperature-controlled water to external heat exchangers or warming/cooling blankets through closed circuits.

Although the water in the circuits does not come into direct contact with the patient, there is the potential for contaminated water to enter other parts of the device or transmit bacteria through the air, via the device's exhaust vent, into the environment and to the patient, the FDA notes in a safety communication posted on its website, Between January 2010 and August 2015, the FDA received 32 reports of patient infections associated with heater-cooler devices or bacterial heater-cooler device contamination, with 25 reported this year.

"Some reports describe NTM infections related to cardiothoracic surgeries, but other reports do not specify the procedure the patient was undergoing," the FDA notes. Eight reports were related to three events describing patient infections occurring in US healthcare facilities, whereas the other 24 reports involved facilities outside the United States, mostly in Western Europe.

In some cases, patients presented with infections several months to years after their surgical procedure. The FDA is not aware of NTM infections acquired by hospital staff.

The FDA says it is "actively" monitoring the situation and will provide updates as appropriate.

The aim of today's safety communication is to "heighten awareness about infections associated with heater-cooler devices and steps health care providers and health facilities can take to mitigate risks to patients," they say.

Recommendations

In addition to following standard precautions, the FDA recommend that healthcare facilities and staff using heater-cooler devices consider implementing the following measures to reduce risk to patients:

Strictly adhere to the cleaning and disinfection instructions provided in the manufacturers device labeling. Ensure you have the most current version of the manufacturers' instructions for use readily available to promote adherence.

Do not use tap water to rinse, fill, refill or top-off water tanks, as this may introduce NTM organisms. Use only sterile water or water that has been passed through a filter of less than or equal to 0.22 microns. When making ice needed for patient cooling during surgical procedures, use only sterile water or water that has been passed through a filter of less than or equal to 0.22 microns. Deionized water and sterile water created through reverse osmosis is not recommended because it may promote corrosion of the metal components of the system.

Direct the heater-cooler's vent exhaust away from the surgical field to mitigate the risk of aerosolizing heater-cooler tank water into the sterile field and exposing the patient.

Establish regular cleaning, disinfection, and maintenance schedules for heater-cooler devices according to the manufacturers' instructions to minimize the risk for bacterial growth and subsequent patient infection.

Develop and follow a comprehensive quality control program for maintenance, cleaning, and disinfection of heater-cooler devices. Your program may include written procedures for monitoring adherence to the program and documenting set up, cleaning, and disinfection processes before and after use.

Immediately remove from service heater-cooler devices that show discoloration or cloudiness in the fluid lines/circuits, which may indicate bacterial growth. Consult your hospital infection control officials to perform the appropriate follow-up measures and report events of device contamination to the manufacturer.

Consider performing environmental, air, and water sampling and monitoring if heater-cooler contamination is suspected. Environmental monitoring requires specialized expertise and equipment to collect and process samples, which may not be feasible in all facilities.

Healthcare facilities should follow their internal procedures for notifying and culturing patients if they suspect infection associated with heater-cooler devices.

The present invention addresses the aforementioned issues by providing a patient warming bed or blanket that is heated by the circulation of controlled warm air. The warming system circulates all of the warmed air within a closed circuit, so that no warmed air is released outside the closed warm air circulating system. This absence of release of warmed air prevents circulating air currents that may bring microbes to open wounds of a patient.

The closed circuit of the warming system is sterilized with antimicrobial disinfectant spray or atomized mist. The warm air contained in the closed circulating system is sterile. At the end of use of the bed or blanket, the system can be sterilized with antimicrobial disinfectant atomized mist and the disposable bed or blanket discarded.

The closed circuit forced hot air warmer consists of a blower connected by flexible conduit using quick connect couplings to a terminal device, which may be a blanket or a mattress that is not an open tent. The air that enters the terminal device passes through a HEPA filter with a pore size less than 0.22 microns to catch any bacteria or particles in the incoming airflow. The warm air passes through a structured chamber, or a folded tube within the chamber, so that the blanket or mattress is filled with air that passes slowly through the device to an outflow port and returns back to the blower in a completely closed system. There are no apertures to release warm air and no air leaks from the system, avoiding possible turbulence and air currents in the operating room. The internal chamber structure insures that warm air is not shunted to the outflow port, but rather fills the entire chamber, no that the entire device remains warm, transmitting heat to the patient by direct contact and maintaining body temperature. The return air conduit is detachable from the device, as well. The blanket or mattress, therefore, remains a simple, inexpensive device and is suitable for disposal after use.

The HEPA filters at the inflow and outflow portals of the blower and the fact that each disposable pad is clean help to avoid bacterial contamination. The unique design of the system makes sterilization of the air channels in the blower and the connecting tubes easy to perform. The detached ends of the flexible inflow and outflow lines are each connected to a small (detachable) chamber containing a well. A measured amount of liquid disinfectant is introduced through a separate port and the blower is turned on. The circulating air will take up the disinfectant, which will he carried through the system as an aerosol. After a brief period, all internal surfaces are disinfected. A second aliquot of STERILE distilled water can be added later to rinse out the system. Following the disinfection step; the two conduits are disconnected. Any aerosol (mostly water) that remains is blown out and the sterilized system is ready for use. In addition, a sponge or other trap may be employed to capture the water.

A filtered port allows ambient air to enter the blower at the beginning of a cycle. When the system has been filled and air begins to return via the outflow conduit, the entry portal is capped and only air from the outflow conduit can enter the blower for recirculation.

Briefly stated, the closed circuit forced hot air warmer of patient beds and blankets with improved sterility provides hot air for warming a patient bed or blanket, preventing hypothermia of the patient that may significantly increase healing time periods. Warm air is supplied from a blower the inlet and outlet ports of which are guarded with a HEPA filter having a pore dimension less than 0.22 microns to prevent the entry of microorganisms or dust particles. The temperature of warm air, its pressure and flow rate are controlled by a control panel set by the operator of the device. When used to warm the bed of the patient, the air pressure within the mattress helps to support the patient's body weight. Being a closed system, the pressure can be readily increased according to the weight and size of the patient. The flow rate determines how quickly the warmed air is delivered to the patient and is related to the rotational rate of a blower motor.

FIG. 1 illustrates at 100 a system for delivering warm air to patient beds and blankets in a closed circulating circuit. The closed circuit warm air delivery system comprises a blower 101 with microprocessor controlled temperature, pressure and flow control that has input and output ports each guarded by HEPA filters. The blower output port is connected to the input port of patient bed or blanket 102 using by flexible tubing with quick release connectors 104. The output port of the patient bed or blanket is connected to the input port of the blower 101 using flexible tubing again with quick release connectors 104. The microprocessor control panel is shown at 105. The microprocessor controls the warm air temperature at 105*a* warm airflow rate at 105*b* and warm air pressure at 105*c*. The warm airflow path is therefore a continuous closed circuit with no warm air escape location. The airflow rate is proportional to the speed of rotation of the blower motor. The pressure in the patient bed, which is capable of supporting the body weight of the patient, is also controlled by the blower fan motor speed. The electrical current supplied to the heating elements controls the warm air temperature.

FIG. 2 illustrates at 200 the blower with air warmer machinery and flexible tubes used being sterilized by the antimicrobial mist generator. The blower with air warmer machinery is shown at 101 with HEPA filters both at inlet and outlet. The output of the blower is connected to the inlet of the antimicrobial mist generator 103 using a flexible hose provided with quick release couplings. The output of the antimicrobial mist generator 103 is connected to the inlet port of the blower 101 using a flexible hose provided with quick release couplings. The antimicrobial solution in the antimicrobial mist generator is atomized and circulated in this closed path for a preselected time period, which may be as long as 15 minutes, disinfecting circuit sterilizing the blower with air warming machinery 101 and all the flexible hoses in the system. At the end of this disinfecting step, the quick release couplings are disconnected and any moisture present in the blower 101 and flexible hoses is blown out through the outlet hose. Any excess water can be blown into a dry sponge.

FIG. 3 illustrates at 300 the details of the microprocessor controlled blower with warm air delivery 101. As illustrated, the blower has input port 302 and output port 303 both provided with HEPA filters. The quick release connectors of the flexible hose are shown at 104. The warm air flow bath is indicated by the arrows. The blower with warm air delivery has a blower fan and electrical heating elements sensors for air temperature, air pressure and air low rate communicating with the microprocessor control as shown in FIG. 1

FIG. 4 illustrates at 400 the microprocessor controlled antimicrobial mist generator, which is only used to achieve internal sterilization of the blower warm air machinery 101 and all the flexible hoses used. The mist generator is filled with a capsule 402 that has the antimicrobial liquid sealed with gasket 403, which is atomized by the flow of warm air through the input port and is delivered to the output port. The microprocessor according to FIG. 2 turns on the antimicrobial mist spray during initial set up to sterilize the interior surfaces of blower and flexible tubes. When the sterilization operation is complete, an aliquot of sterile distilled water is introduced and any residual disinfectant is removed in the circulated water vapor. Quick release couplings 104 connect the flexible hoses to the inlet and outlet of antimicrobial mist generator 103. The mist generator is disconnected from both flexible hoses and the system dried internally by running the blower. Any excess water can be blown out into a clean sponge.

Figure 5:
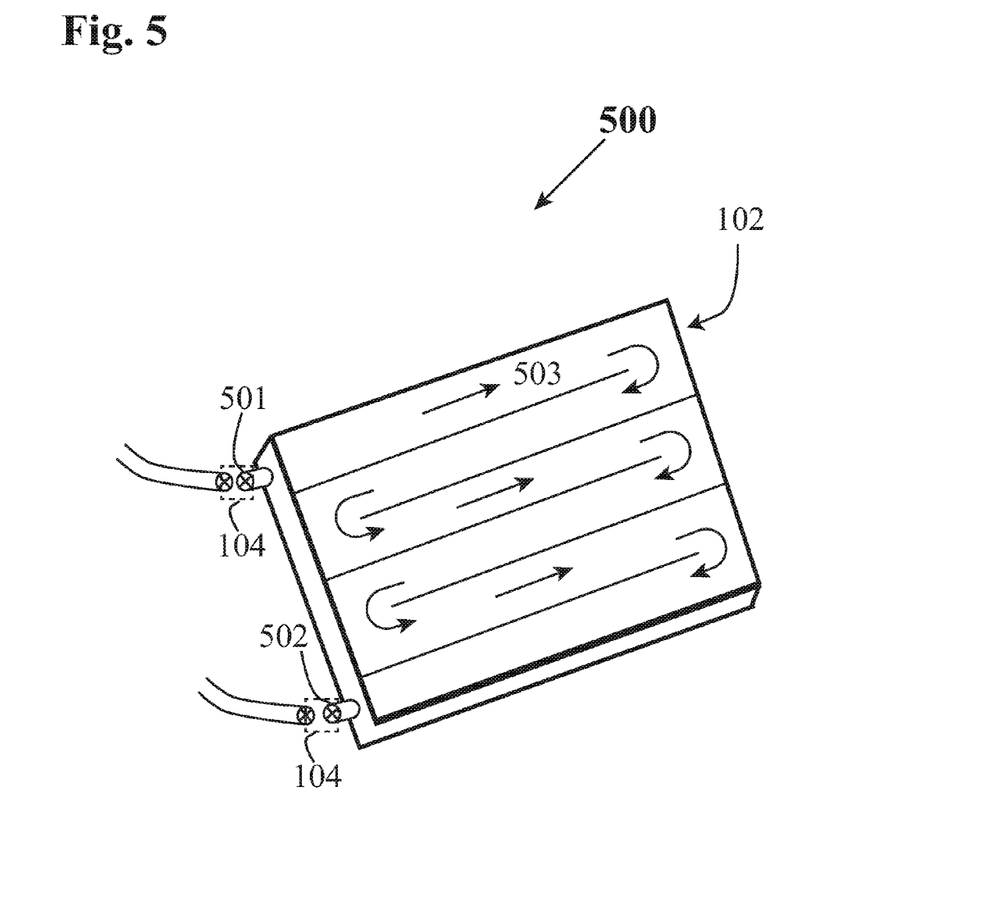
FIG. 5 illustrates the patient mattress or blanket.

FIG. 5 illustrates at 500 the patient bed or blanket 102. The inlet of warm air into the bed or blanket is shown at 501. The patient bed or blanket has a plurality of interconnected airflow paths indicated by arrows shown at 503. The outlet of the patient bed or blanket 102 is shown at 502. The connection of flexible hose to the inlet and outlet is done using quick release couplings 104.

Figure 1:
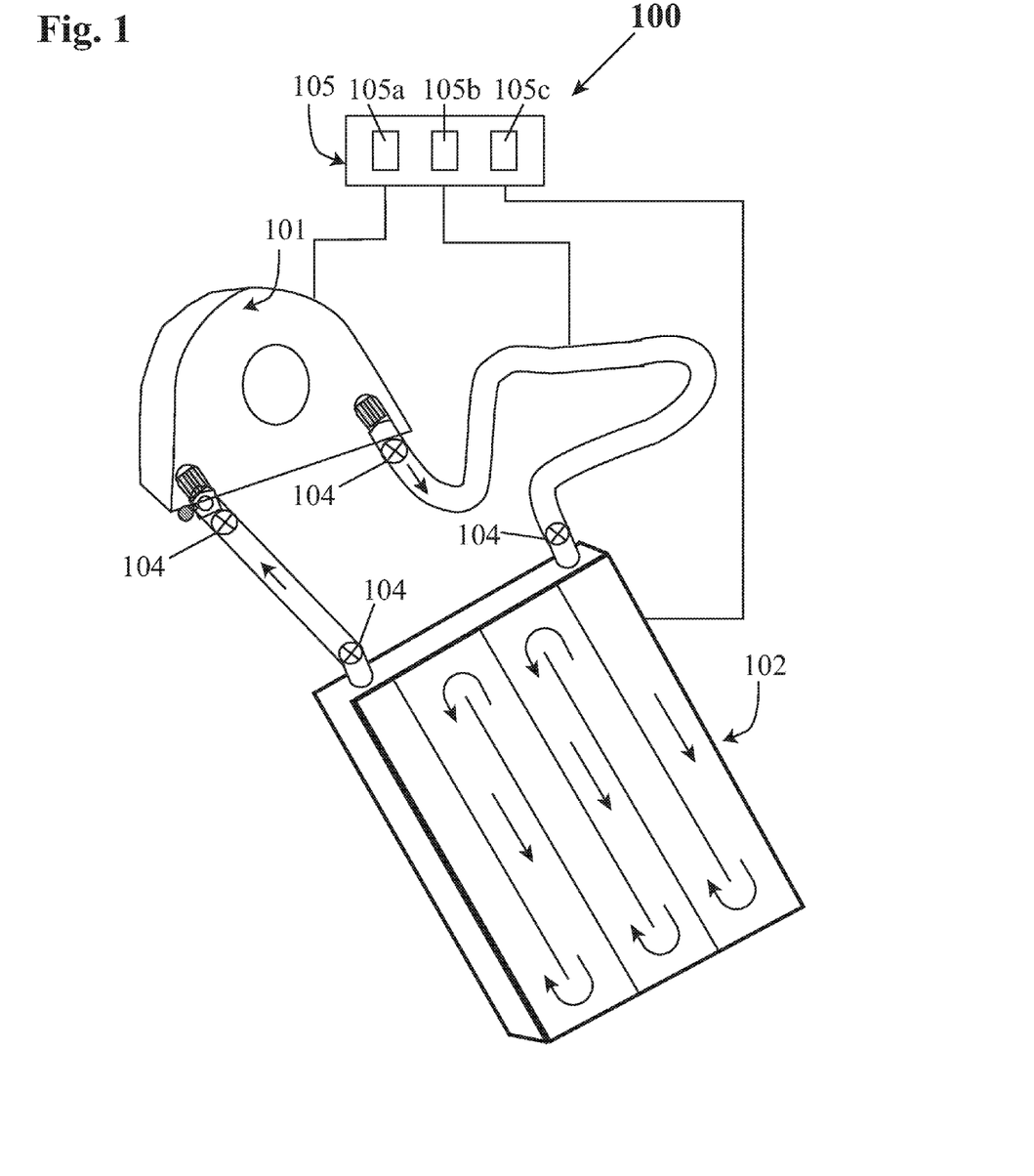
FIG. 1 illustrates a system for delivering warm air to patient beds and blankets in a closed circulating circuit.
Figure 2:
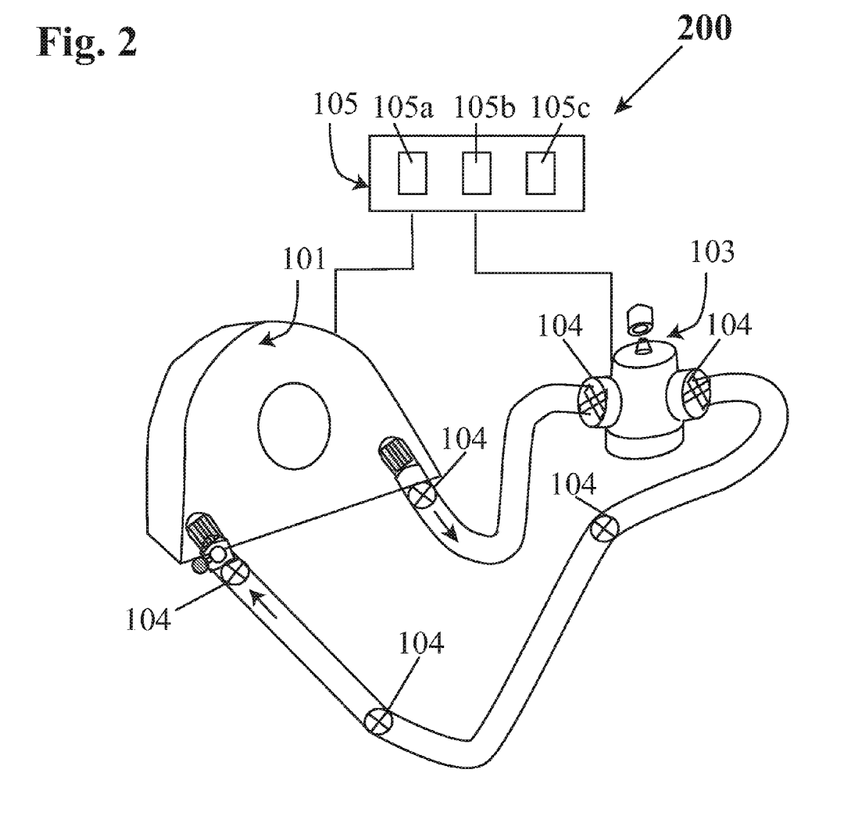
FIG. 2 illustrates the blower with air warmer machinery and flexible tubes being sterilized by the antimicrobial mist generator.
Figure 3:
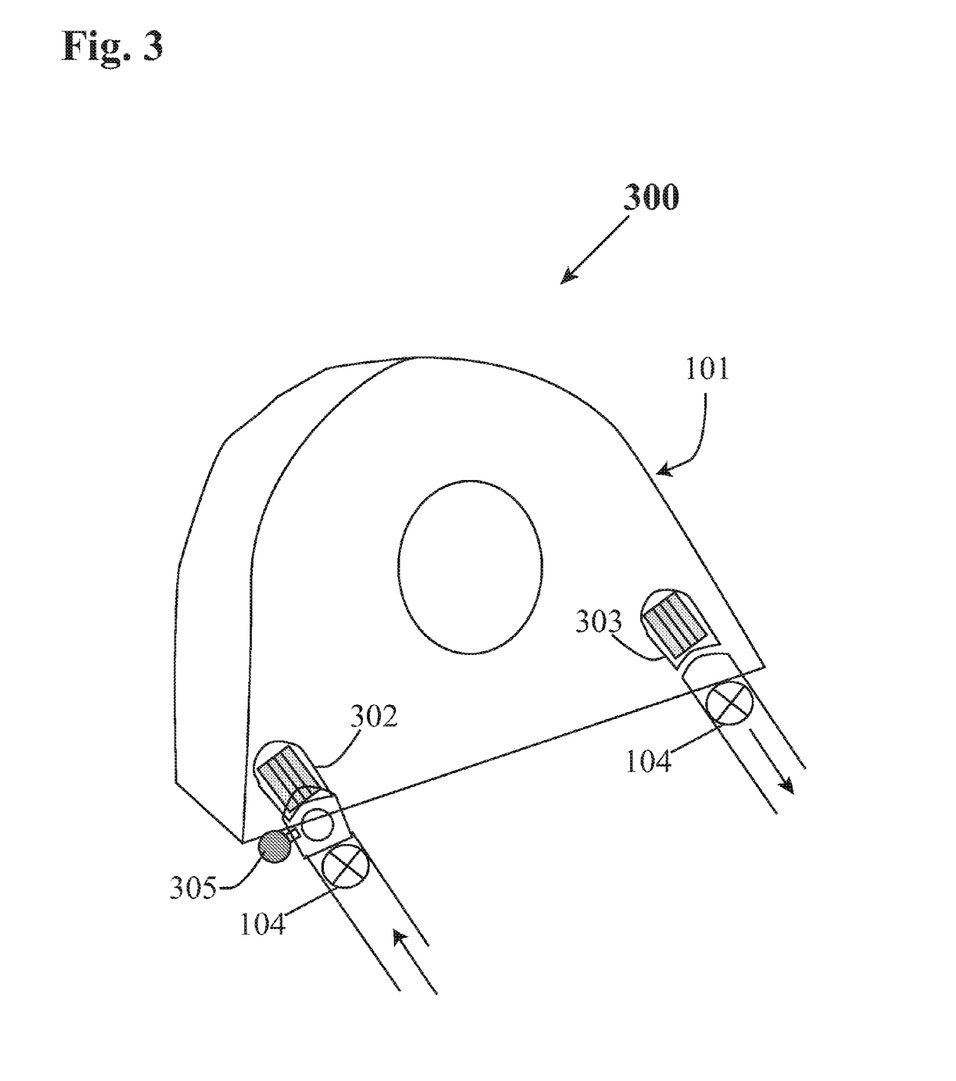
FIG. 3 illustrates the details of the microprocessor controlled blower with input port 202 and an output port, both provided with HEPA filters.
Figure 4:
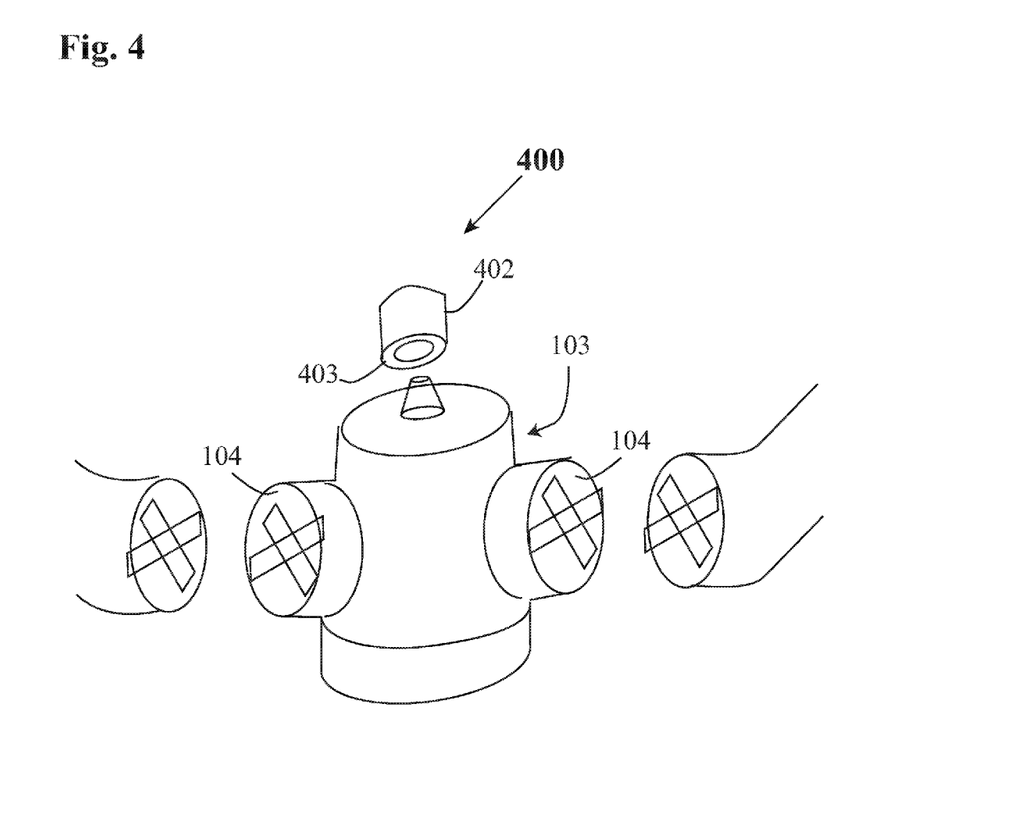
FIG. 4 illustrates the microprocessor controlled antimicrobial mist generator.
Figure 6:
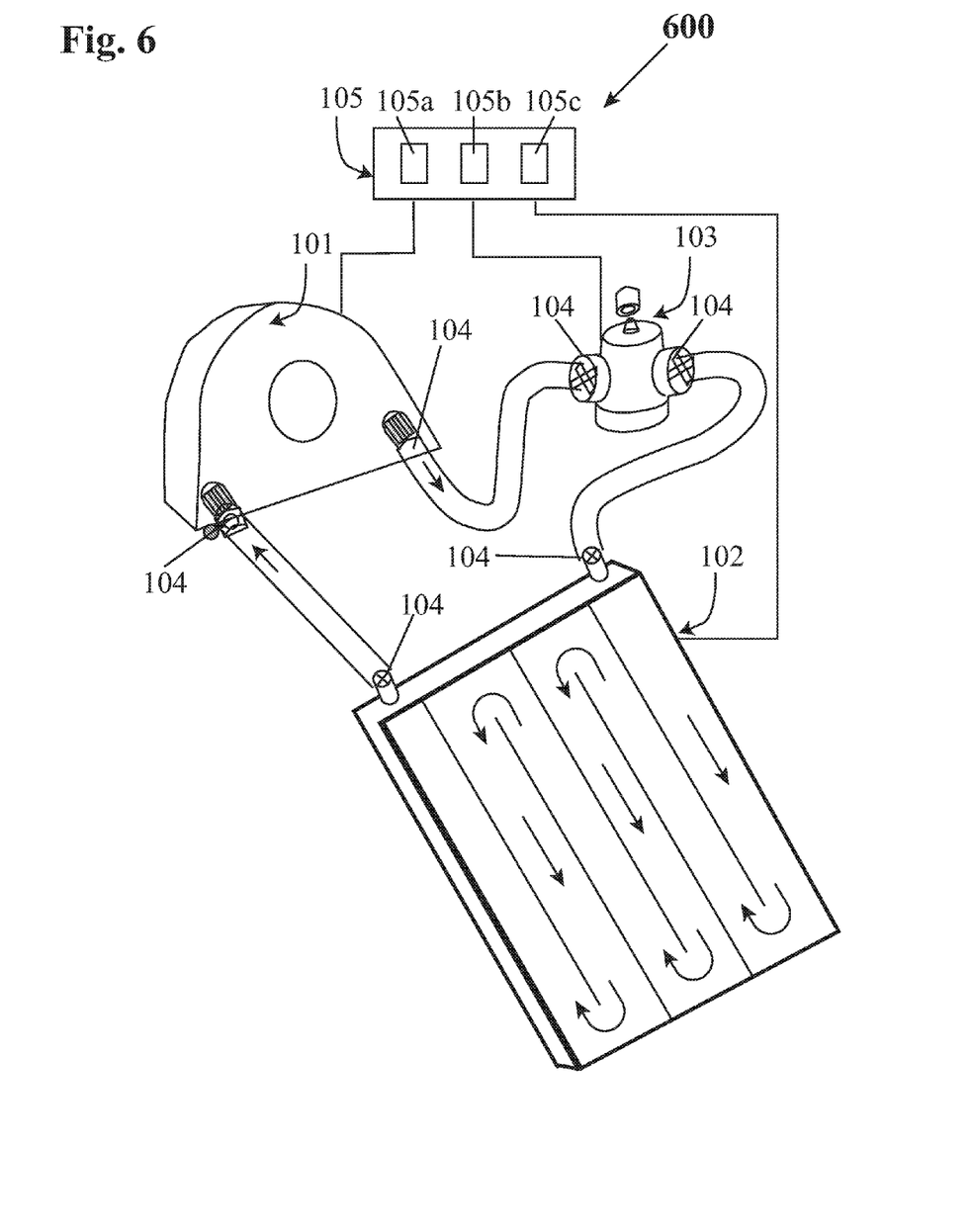
FIG. 6 illustrates the sterilization process of the patient bed or blanket prior to disposal.

FIG. 6 illustrates at 600 an optional arrangement for the sterilization process of patient bed or blanket. This is similar to FIG. 1 except that the antimicrobial mist generator 103 is inserted between the blower warm air machinery 101 and the patient bed or blanket 102 and a closed circuit is formed using flexible hoses with quick release connectors 104. When used prior to disposal, the sterilization process is run for about 15 minutes and the sterilized patient bed or blanket is discarded.

In its preferred embodiment, the system for closed circuit forced hot air warmer of patient beds and blankets with improved sterility of the present invention comprises:
1) a blower with controlled air heating capability having an input and an output opening, each opening being provided with a HEPA filter;
2) said HEPA filters having pore openings less than 0.22 microns capable of filtering microbes and dust particles;
3) said output opening being connected to an input connect on of a bed or blanket using a flexible hose with quick release connector;
4) said patient bed or blanket having an output that connects the ex warm air to the input of said blower, said connection being made with a flexible hose and quick release connector;
5) the entire flow path of warmed air being a closed circuit with no discharge of warmed air surrounding the patient within the operating room;
6) a flexible hose able to connect to an antimicrobial mist generator 8 with a quick release connector;
7) said antimicrobial mist generator being connectable to the return blower with a quick release connector;
8) said antimicrobial mist generator being detached during warming of the patient bed or blanket by passage of warm air from said blower;
9) said antimicrobial mist. generator, being reconnected to the blower by the output and return hose, being tuned on as needed for internal cleaning after the safe disposal of said patient bed or blanket;
whereby said system for said closed circuit forced hot air warmer of patient beds and blankets with improved sterility prevents the microbial contamination of the patient or hospital workers in the operating room.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:
1. A system for closed circuit forced hot air warmer of patient beds and blankets with improved sterility, comprising:
 a) a sterilized blower with microprocessor controlled air heating capability having an input and an output opening, each opening being provided with a high-efficiency particulate air filter;
 b) said high-efficiency particulate air filters having pore openings less than 0.22 microns capable of filtering microbes and dust particles;
 c) said output opening of said sterilized blower being connected to an input connection of a bed or blanket using a sterilized flexible hose with quick release connector;
 d) said bed or blanket having an output that is connected to the input of said sterilized blower with a second sterilized flexible hose with quick release connector;
 e) said sterilized blower being appointed to circulate heated air within said bed or blanket, thereby forming a closed circuit without discharging said heated air into the area surrounding a patient or into an operating room; and
 f) sterilization of said sterilized blower and said sterilized flexible hoses being accomplished by connecting said output opening of said sterilized blower to said inlet of a microprocessor controlled antimicrobial mist generator and connecting an output of the microprocessor controlled antimicrobial mist generator to said inlet opening of said sterilized blower, thereby forming a closed circuit;
whereby said system for said closed circuit forced hot air warmer of patient beds and blankets with improved sterility prevents microbial contamination of said patient or of hospital workers by unsterile air currents generated by warm air released into the operating room.

2. The system for closed circuit forced hot air warmer of patient beds and blankets with improved sterility as recited by claim 1, wherein sterilization of said sterilized blower and said sterilized flexible hoses is accomplished by running a sterilization cycle for a preselected time period.

3. The system for closed circuit forced hot air warmer of patient beds and blankets with improved sterility as recited by claim 2, wherein said preselected time period is less than 15 minutes.

4. The system for closed circuit forced hot air warmer of patient beds and blankets with improved sterility as recited by claim 1, wherein the sterilized blower and said sterilized flexible hoses are cleared of accumulated moisture by running the blower with the microprocessor controlled antimicrobial mist generator disconnected.

5. The system for closed circuit forced hot air warmer of patient beds and blankets with improved sterility as recited by claim 1, wherein said microprocessor controlled antimicrobial mist generator controls the amount of antimicrobial delivered for atomization into the antimicrobial mist generator.

6. The system for closed circuit forced hot air warmer of patient beds and blankets with improved sterility as recited by claim 1, wherein said sterilized blower with controlled air heating capability controls warm air temperature, warm air flow rate and air pressure.

7. The system for closed circuit forced hot air warmer of patient beds and blankets with improved sterility as recited by claim 1, wherein an interior of said sterilized blower and said flexible hoses are sterilized by connecting to said microprocessor controlled antimicrobial mist generator for a preselected time after disposal of the bed or blanket.

8. The system for closed circuit forced hot air warmer of patient beds and blankets with improved sterility as recited by claim 7, wherein said bed or blanket is connected to said microprocessor controlled blower with controlled air heating capability and a microprocessor controlled antimicrobial mist generator with flexible quick connect hoses, effecting sterilization of the bed or blanket, and thereby protecting workers from exposure to microbes.

9. The system for closed circuit forced hot air warmer of patient beds and blankets with improved sterility as recited by claim 7, wherein said preselected time is less than 15 minutes.

* * * * *